United States Patent [19] [11] Patent Number: 5,002,735
Alberhasky et al. [45] Date of Patent: Mar. 26, 1991

[54] TISSUE ANALYSIS DEVICE

[75] Inventors: Mark T. Alberhasky, 820 Mooreland, Bowling Green, Ky. 42101; James D. Riehm, Bowling Green, Ky.

[73] Assignee: Mark T. Alberhasky, Bowling Green, Ky.

[21] Appl. No.: 217,935

[22] Filed: Jul. 12, 1988

[51] Int. Cl.⁵ .................................................. B01L 3/00
[52] U.S. Cl. ...................................... 422/99; 422/102; 422/104; 422/58; 422/82.05; 422/82.08; 436/63; 436/64; 436/813; 435/287; 435/310; 378/28
[58] Field of Search ................... 422/99, 102, 104, 68, 422/292, 300, 58; 436/63, 64, 813; 435/287, 310; 378/28

[56] References Cited

U.S. PATENT DOCUMENTS 2,737,594  3/1956  Katz et al. ............................. 250/53
4,387,990  6/1983  Yazawa et al. .................. 422/102 X
4,562,045  12/1985  Murata ................................. 422/102
4,563,768  1/1986  Read et al. ............................ 378/37
4,691,333  9/1987  Gabriele et al. ....................... 378/37
4,714,595  12/1987  Anthony et al. ..................... 422/294
4,734,260  3/1988  Lautenchlager ....................... 422/58
4,761,378  8/1988  Godsay ................................. 435/293

Primary Examiner—Robert J. Warden
Assistant Examiner—Lynn M. Kummert
Attorney, Agent, or Firm—Theresa F. Camoriano

[57] ABSTRACT

A tissue analysis device includes first and second plates which are rigid and radiographically transparent, at least one of the plates defining a plurality of pinholes arranged in an evenly spaced pattern to form a rectangular grid, with at least one of the plates including coordinate markings which can be seen both optically and radiographically to create a rectangular coordinate system for defining each section of the grid.

14 Claims, 3 Drawing Sheets

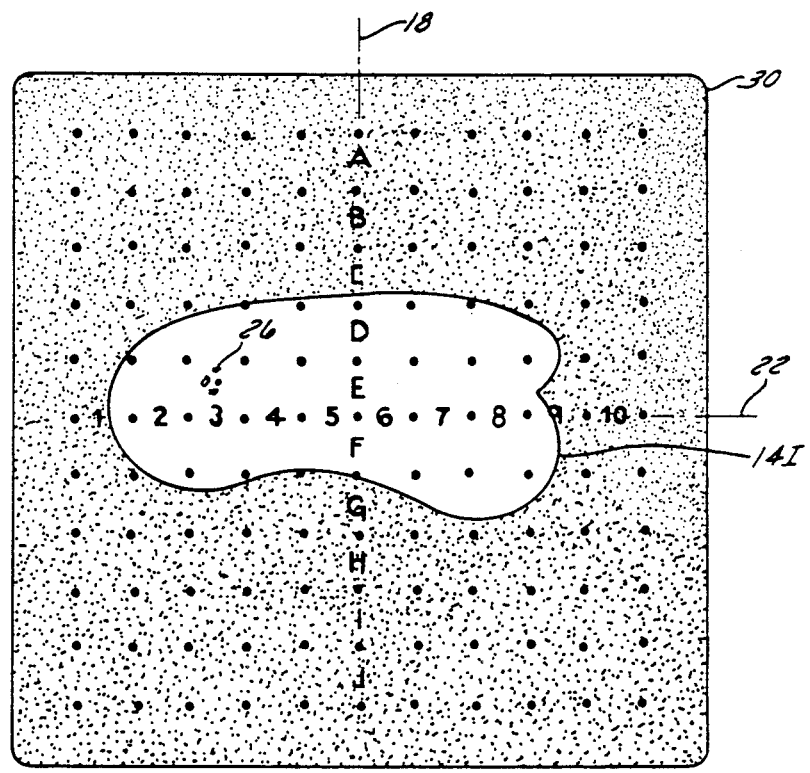
FIG. 5
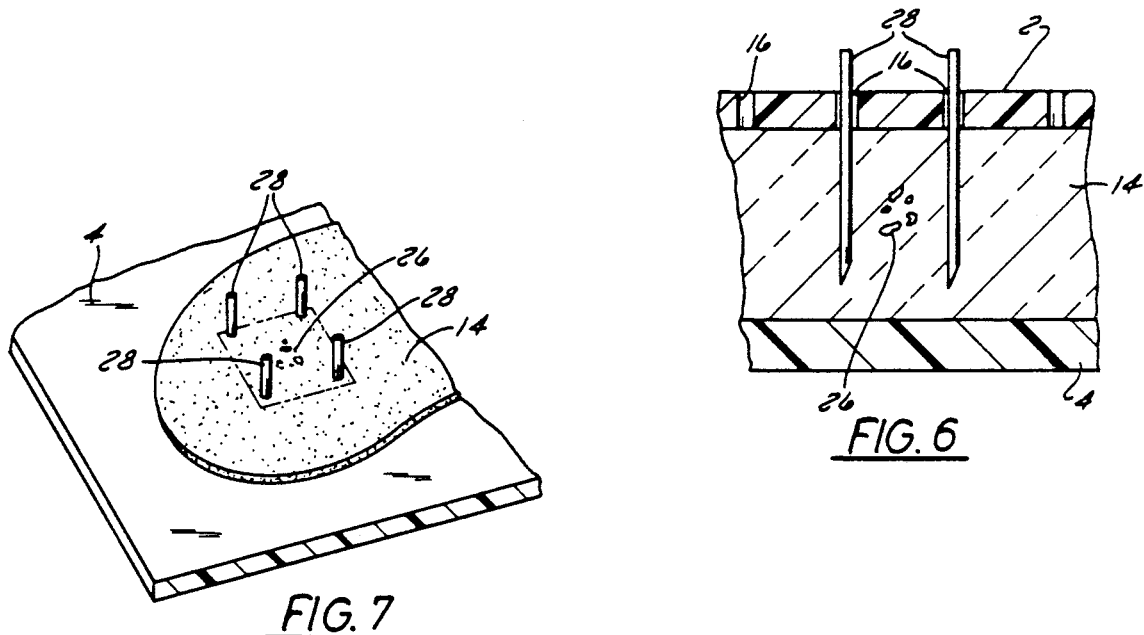
FIG. 6
FIG. 7

TISSUE ANALYSIS DEVICE

BACKGROUND OF THE INVENTION

This invention relates to the fields of pathology and radiology, and, in particular, to a device for finding small abnormalities in excised tissue The current practice of radiology includes performance of mammography, a form of breast x-ray examination which allows detection of very small abnormal lesions, some of which are potentially cancerous. The current practice of pathology includes examination of excised breast tissue in order to demonstrate and assess the mammographic abnormality. The small size of these lesions is correlated with a very early stage of development, which affords a higher chance for cure if cancerous. These small lesions have the characteristic of being non-palpable (cannot be felt with examination by the hand). In addition, these lesions are usually small enough that they cannot be seen by naked eye inspection of the actual tissue.

Detection of a lesion by mammography, its surgical excision, and diagnosis of its cancerous potential by a pathologist form the basis upon which recommendations for patient treatment are made. In order for these diagnostic/therapeutic procedures to be effective, (a) the lesion must be found by mammography, (b) the surgeon must excise the appropriate portion of breast tissue containing the abnormality and (c) the pathologist must isolate the specific abnormality in question and examine it microscopically to determine its nature. Failure to adequately perform any aspect of this process may result in unsatisfactory examination of the patient with potentially serious consequences in regard to choosing a subsequent treatment plan. Failure to demonstrate the malignant nature of an unexamined lesion could result in undertreatment of the patient resulting in significant morbidity and possibly death.

In order to remove small, non-palpable lesions detected by mammography, a process known as needle localization has been developed. The needle localization procedure entails placement of a thin radiographically opaque metal wire in the patient's breast. This is accomplished by the examining radiologist using x-ray technique to place the localizing wire in close proximity to the target lesion. The proximity of the wire to the lesion can vary considerably depending on the size of the breast being examined, the overall consistency of the breast tissue and the size of the target lesion. The patient then goes to surgery with the localizing wire inserted through the skin into the breast tissue. This serves to delineate the area of tissue which the surgeon then excises in order to remove the target lesion.

The actual volume of tissue surgically removed will vary greatly, influenced again by factors including breast size, tissue consistency, lesional size and technique of the operating surgeon. A "small" needle localization biopsy specimen may be 6-7 centimeters (cm) in length, 3-4 cm in width and 2-3 cm high. However, biopsy specimens ranging up to as large as 10-12 cm in greatest dimension are not uncommon.

Because the size of the target lesion may be as small as 0.1 cm, it becomes readily apparent that finding the abnormal tissue within the relatively large volume of tissue removed can be difficult. The difficulty of this task is better appreciated when one considers that the lesion is generally not detected by visual inspection or touch due to its dimensions. Once excised, the tissue specimen is then reexamined mammographically to determine whether or not the abnormal area has been included in the tissue removed. A "specimen" mammogram (as opposed to a "patient" mammogram) is made and compared to the original patient mammogram. This specimen image will show the lesion as well as the localizing wire. Once removal is confirmed, the patient, usually under general anesthesia, can be awakened and released from care following appropriate observation. The specimen is then sent to the Pathology department for study.

Tissue analysis by the pathologist includes two separate but interrelated phases of examination, gross and microscopic study. Gross examination is that phase which includes physically handling the tissue and, by visual inspection of its character, selecting portions of the tissue which are then processed for further study. For specimens which exceed 1-2 cm in dimension, this generally implies selection of specific tissue samples which are representative of the disease process. These samples are then processed to yield materials, tissue sections on glass slides, which can be examined by microscope and from which a diagnosis is rendered.

Bearing in mind that microscopic examination of the mammographic lesion is a critical step in the patient treatment process, a pathologist currently uses one of several techniques to grossly examine the tissue specimen in an effort to ensure that the target lesion is submitted for microscopic study. The specimen can be submitted in its entirety so as to include all tissue removed. This approach will often yield in excess of 50 tissue samples to be processed and for most institutions would create demands on laboratory resources which make it an impractical alternative.

The generally accepted approach is to examine the tissue using its specimen mammogram as a reference, and, through use of perceived landmarks, including the wire and various distinguishing features in the outer contours of the specimen, select and submit enough tissue so as to reasonably expect inclusion of the lesion. In practical terms, precise submission of the lesional tissue can be difficult due to change in position of the specimen between the time its specimen mammogram is prepared and gross examination is performed, due to lack of definitive reference markings on the mammogram or specimen to use during tissue selection and due to the fact that the wire marker may be located a substantial distance from the lesion. An additional approach is to submit the specimen to the pathologist twice, initially to be divided into a number of smaller pieces which are then re-examined by x-ray. The smaller specimen pieces are then sent back to the pathologist with the second specimen film which ideally localizes the abnormality to a smaller volume of specimen tissue. This technique requires repeat examinations by both the radiology and pathology departments. This approach may reduce but does not completely eliminate the basic problems described above.

These factors collectively make examination of such specimens a difficult task. If the lesion is, despite usual and customary technique, not submitted, or if a second incidental lesion is studied and misinterpreted as representing the target lesion, an erroneous diagnosis may be rendered. The present invention addresses these practical concerns and offers greatly improved potential for precise submission of lesional tissue.

SUMMARY OF THE INVENTION

The present invention provides a means for systematically locating a small lesion/abnormality within a larger tissue specimen so that the lesion can be isolated with a very high degree of confidence and examined.

The present invention provides a means for immobilizing the tissue during the period between specimen mammography and gross analysis, eliminating movement and changes in orientation which, in current practice, make specimen examination difficult.

The present invention provides a coordinate grid system to uniquely identify the location of the lesion.

The present invention increases the potential for accurate correlation between patient mammography and pathologic diagnosis, thus improving the standard of patient care in regard to diseases of the breast.

The present invention may, of course, also be used to improve analysis of other tissue types containing small radiodensities.

BRIEF DESCRIPTION OF THE DRAWINGS

FIG. 5 is a top plan view of a developed x-ray film prepared from the tissue sample and apparatus shown in FIG. 2.

FIG. 6 is an enlarged, broken away, side sectional view of the device and tissue sample as shown in FIG. 3, with wires inserted through the pin holes in the top plate to locate the lesion.

FIG. 7 is a broken away top perspective view of the bottom plate, tissue sample, and wires isolating the lesion, with dotted lines indicating where the pathologist will cut to obtain his tissue segment for analysis.

DESCRIPTION OF THE PREFERRED EMBODIMENT

Figure 1:
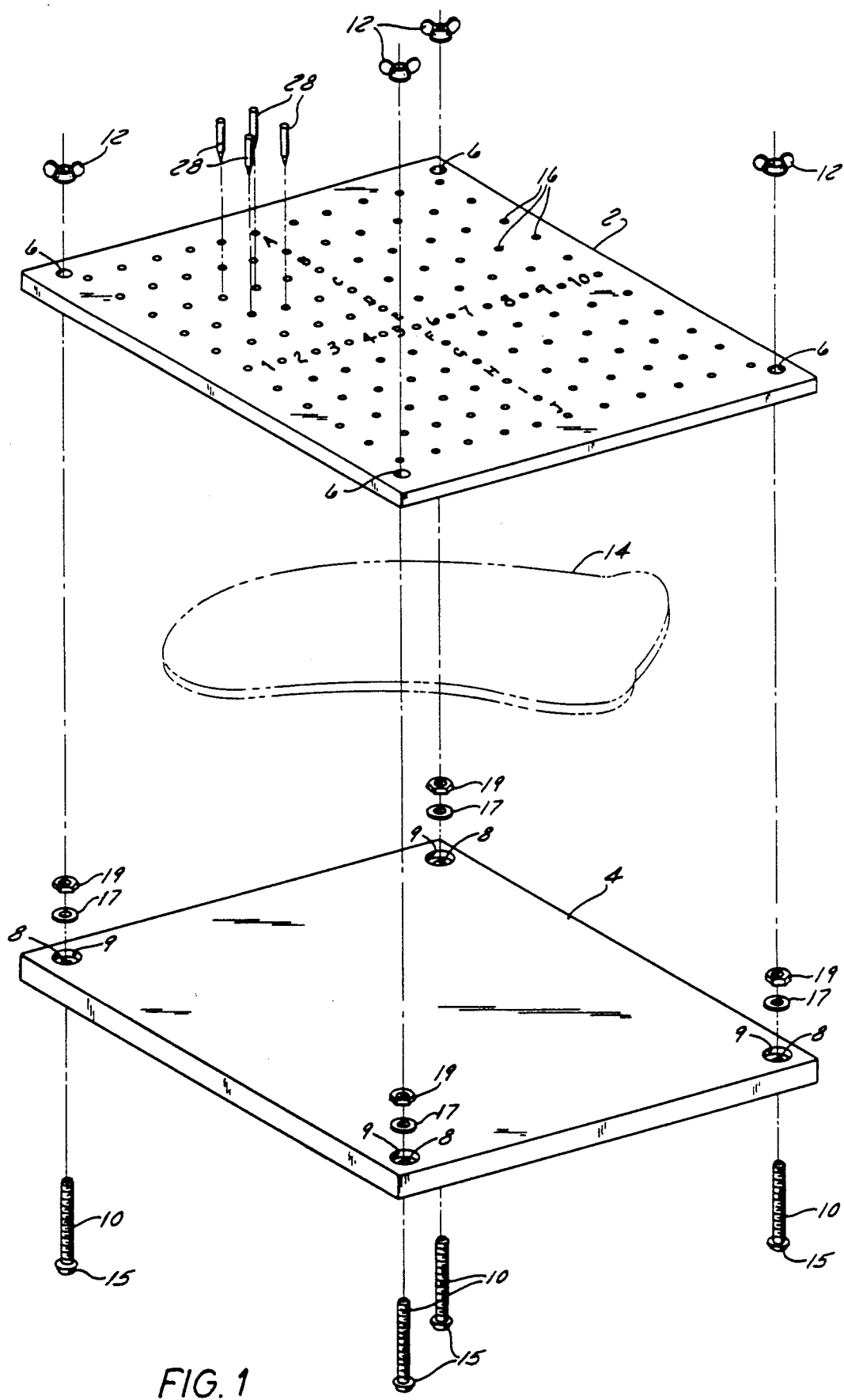
FIG. 1 is an exploded perspective view of the present invention, with a tissue sample located between upper and lower plates.

As shown in the drawings, the present invention includes two relatively rigid plates or sheets 2, 4. Both of the sheets 2, 4 are made of a material that is both radiographically and optically transparent. The tissue analysis device shown in these drawings is made of clear cast acrylic sheet. Each sheet is approximately ten inches wide and ten inches long. The top sheet 2 is approximately one-quarter (¼) inch thick, and the bottom sheet is approximately three-eights (⅜) inches thick. Both plates 2, 4 have larger holes 6, 8 in their four corners. These corner holes (or fastener holes) 6, 8 are located so that the fastener holes 6 in the top sheet 2 can be aligned with the fastener holes 8 in the bottom sheet 4. In order to clamp the two sheets 2, 4 together with a tissue sample between them bolts or fasteners 10 (each of which has a head 15) are inserted through the larger corner holes 8 of the bottom sheet 4 and fixed in place with respect to the bottom sheet 4 with the washers 17 and hex nuts 19. The washers 17 and hex nuts 19 are recessed into the enlarged portions 9 of the corner holes 8. Then the bolts are inserted through the aligned corner holes 6 in the top sheet 2 and tightened down with wing nuts 12 to cause the plates 2, 4 to exert a compressive force on the tissue sample 14. The bolts have a fairly close tolerance fit in the holes 6, 8, so the entire assembly is maintained in close alignment from the time the wing nuts are tightened until they are removed and the compressive force is released.

Figure 2:
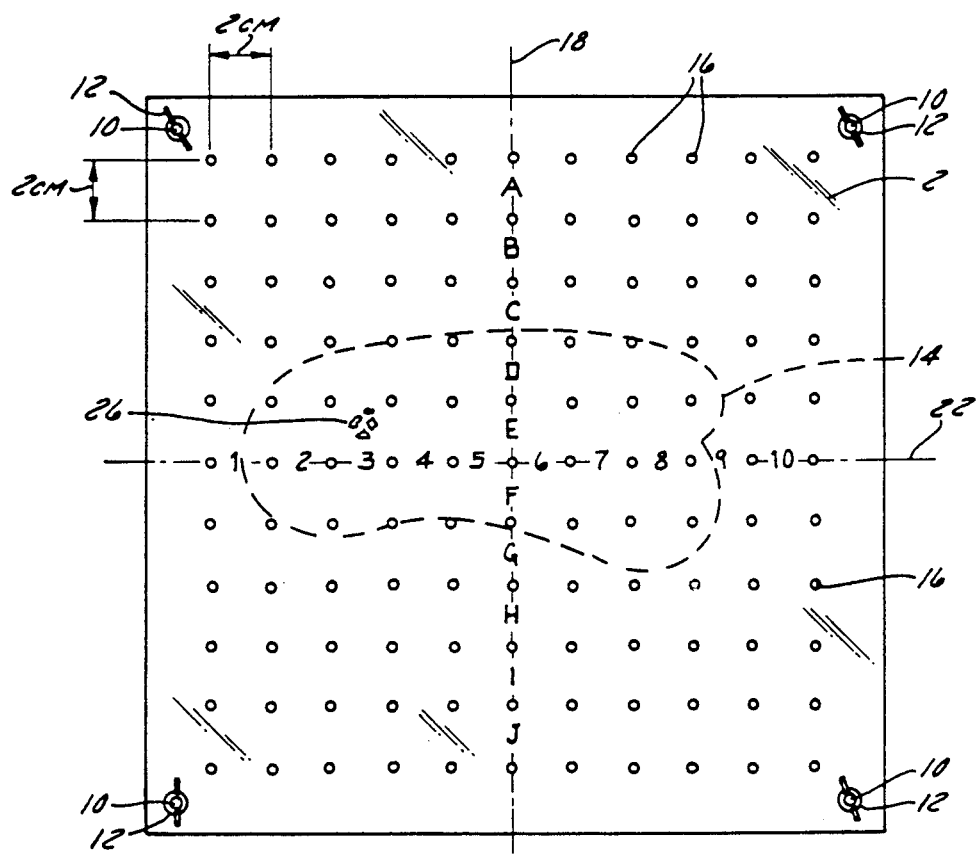
FIG. 2 is a top plan view of the assembled invention shown in FIG. 1.
Figure 3:
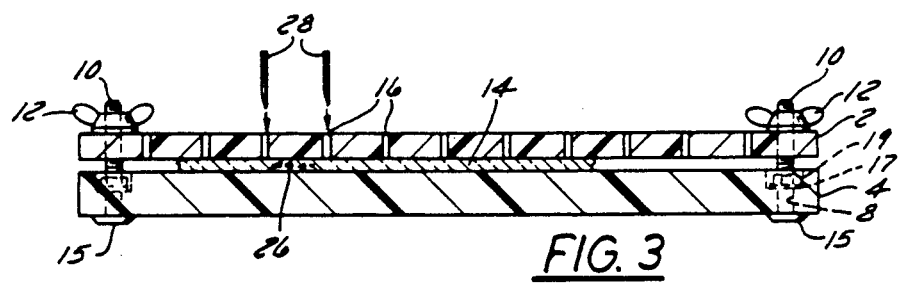
FIG. 3 is a side sectional view of the invention shown in FIG. 2.
Figure 4:
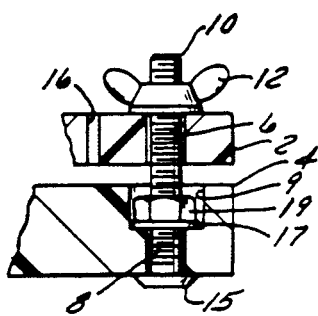
FIG. 4 is an enlarged, broken away side sectional view of the invention shown in FIG. 2 showing the bolting arrangement used in the present invention.

In the top sheet 2 are located very small holes (pinholes) 16 which are evenly spaced at two-centimeter intervals to form a rectangular grid system. In this embodiment, the dimensions of the plates are rectangular, but a rectangular grid system could exist on any shape of plate as long as it is based on perpendicular axes with evenly-spaced holes. A central vertical axis 18 (shown in phantom in FIG. 2) is marked with coordinates in the form of letters A through J, located between the pinholes 16. A central horizontal axis 22 (shown in phantom in FIG. 2) is marked by coordinates in the form of the numbers 1 through 10, again located between the pinholes 16. By means of these coordinates, located on the centrally located vertical and horizontal axes 18, 22, every two centimeter-by-two centimeter square area which is enclosed in a rectangle defined by four pinholes 16 (i.e., every segment of the grid) is uniquely identified by a single combination of one letter and one number. For example, the square "E3" is the position of the abnormality in the x-ray in FIG. 5.

The coordinate markings are placed on the top sheet 2 by engraving or some other technique which decreases the density of the acrylic sheet 2. The engraving can be seen optically, and the decreased density in the shape of the coordinate markings can be seen radiographically, such as on the x-ray film shown in FIG. 5. The coordinates could alternatively be printed on the top sheet 2 using a material that is radiographically opaque. The bottom plate 4 as shown here has no markings or pinholes. However, it is possible to put either markings or pinholes or both on the bottom plate 4.

In order to use the present invention, a sample of tissue 14 which has been removed from a patient is placed between the top and bottom sheets 2, 4 in a central portion of the sheets, so as to be adjacent to the intersection of the axes 18, 22. The bolts 10, which have been affixed to the bottom sheet 4 by means of the washers 17 and hex nuts 19, are fitted through the respective corner holes 6 of the top sheet 2. The wing nuts 12 are tightened down on the bolts 10 to draw the top and bottom plates 2, 4 together. This process immobilizes the specimen, preventing any further movement or changes in orientation of the tissue sample 14 relative to the top and bottom plates 2, 4. It also compresses the specimen 14, reducing its thickness. The reduction in thickness creates several benefits, including improving the quality of radiographic images of the specimen and minimizing the volume of tissue for any given amount of surface area which may be submitted for microscopic study. The tissue sample 14 is now clamped between the two sheets 2, 4 and will remain in the same position relative to the pinholes 16 until it is removed from between the plates 2, 4.

It should be noted that, while the abnormality 26 is shown in FIGS. 2, 3, 6 and 7, it would not actually be visible to a person observing the tissue sample 14 with the naked eye. The abnormality 26 can really be seen only in the x-ray film shown in FIG. 5. However, it is shown throughout the draWings to aid in the discussion of the invention.

The clamped tissue sample 14, located between the top and bottom sheets 2, 4, is then placed in an x-ray device between a source of x-rays and an x-ray recording device such as a film cartridge. (Henceforth, the term "clamped tissue sample" will be understood to mean a unit including the sample 14, the top and bottom plates 2, 4, and any clamping devices such as the bolts 10 and nuts 12 used to hold the plates and tissue sample together.) An x-ray of the clamped tissue sample 14 is then taken. The clamped tissue sample 14 is then removed from the x-ray device.

The x-ray recording, which probably will be in the form of a developed film, is then examined to locate the abnormality. In the present example, the resulting recording is shown in FIG. 5. Once the abnormality 26 is found on the x-ray film, its location is defined in terms of the coordinates which are also shown on the x-ray film. In FIG. 5 it can be seen that the abnormality 26 is located within the grid segment defined by the coordinates "E3". The specimen film 30, with the grid pattern superimposed on the specimen image 14I, and the clamped tissue specimen 14 are then sent to the laboratory for examination by the pathologist.

Now the pathologist can examine the clamped tissue sample 14, which is still held between the plates 2, 4 and locate the abnormality 26 on the actual tissue sample 14 by means of the coordinates marked on the top plate 2. Although the clamped tissue sample may have been transported some distance between the points of x-ray exam and pathologic exam, the coordinates "E3" on the to plate 2 continue to precisely define the location of the lesion, because the relative positions of the tissue sample 14 and top and bottom sheets 2, 4 are the same throughout this process.

The coordinates "E3" are then located on the top plate 2, to define the location of the lesion 26. At this point, marking instruments 28, preferably pins or wires, are inserted into the specimen 14 through the pinholes 16. In this case, wires 28 have been inserted into the four pinholes 16 surrounding the "E3" grid segment to identify the quadrant of specimen tissue which contains the abnormality 26 to be submitted for microscopic study. Once the area of tissue is marked, the top plate 2 can be removed by releasing the wing nuts 12, and the specific quadrant of tissue that has been marked can be excised from the tissue sample 14. The dotted lines surrounding the wires 28 in FIG. 7 indicate where the pathologist might cut the specimen 14 to remove the lesion 26. By cutting around the wires 28 (whose placement is defined by holes 16), the tissue quadrant that is removed is approximately two centimeters by two centimeters and will easily fit into a standard tissue processing cassette.

Since the abnormality 26 is known to be located within this small quadrant of tissue, particularly thorough techniques may be applied to analyze this limited volume of tissue, whereas it would have been impractical to apply these techniques to a larger volume sample. Through the use of the present invention, the pathologist is able to minimize the need to examine the bulk of the tissue sample in order to find the tiny abnormality. While each pathologist will probably develop his own technique for using the present invention, it is clear that use of the present invention improves the potential for correct tissue diagnosis and thereby improves the quality of patient care.

It will be clear to those skilled in the art that modifications may be made to the embodiment described herein without departing from the scope of the present invention.

What is claimed is:

1. A tissue analysis device, comprising:
   first and second plates, made of a material that is rigid and radiographically transparent;
   at least one of said plates defining a plurality of pinholes arranged in an evenly-spaced pattern to form a rectangular grid system;
   at least one of said plates including coordinate markings which are viewable both optically and radiographically to create a rectangular coordinate system for defining each segment of said grid system; and
   clamping means for clamping together said first and second plates, including means for compressing an excised tissue specimen disposed therebetween, wherein said clamping means permits said clamped-together first and second plates to readily be moved into and out of an x-ray machine and onto a lab table.

2. A tissue analysis device as recited in claim 1, wherein said first plate includes said plurality of pinholes and is also optically transparent.

3. A tissue analysis device as recited in claim 2, wherein the first plate also includes the coordinate markings.

4. A tissue analysis device as recited in claim 1 or 3, wherein said coordinate markings are located along central vertical and horizontal axes of at least one plate.

5. A tissue analysis device as recited in claim 4, wherein the coordinate markings along one axis are numbers and the coordinate markings along the other axis are letters, so that each segment of the plate is defined by a unique letter and number combination.

6. A tissue analysis device as recited in claim 5, wherein said plurality of pinholes are spaced approximately two centimeters apart.

7. A tissue analysis device as recited in claim 4, wherein each of said first and second plates defines at least three fastener holes, so that corresponding fastener holes in said first and second plates are aligned to receive a fastener for clamping a tissue sample between said plates.

8. A tissue analysis device as recited in claim 7, and further comprising at least three bolts which are received in said fastener holes with a fairly close tolerance fit.

9. A tissue analysis device as recited in claim 1, wherein said coordinate markings are engraved on one of the plates.

10. A tissue analysis device, comprising:
    first and second plates, made of a material that is rigid and radiographically transparent;
    said first plate defining a plurality of pinholes arranged in an evenly-spaced pattern with respect to perpendicular axes to form a grid;
    at least one of said plates being visually transparent;
    said first plate defining at least three fastener holes, and said second plate defining at least three corresponding fastener holes, whereby said first and second plates may be clamped together with a tissue sample therebetween by means of fasteners passing through the aligned fastener holes in said first and second plates.

11. A tissue analysis device as recited in claim 10, further comprising at least three bolts which are received in said fastener holes for clamping together said first and second plates.

12. A tissue analysis device as recited in claim 10, wherein one of said plates includes coordinate markings along central vertical and horizontal axes, said coordinate markings being located between pinholes and being visible both optically and radiographically.

13. A tissue analysis device, comprising:

first and second plates, having substantially the same size and shape and being made of a material that is rigid and radiographically transparent;

at least one of said plates defining a plurality of pinholes arranged in an evenly-spaced pattern to form a rectangular grid system;

at least one of said plates including coordinate markings which are viewable both optically and radiographically to create a rectangular coordinate system for defining each location in said grid system; and clamping means for clamping together said first and second plates including means for compressing an excised tissue specimen between them, wherein said clamping means permits the clamped-together plates to readily be moved into and out of an x-ray machine and onto a lab table.

14. A tissue analysis device as recited in claim 13, wherein said coordinate markings are formed by etching one of said plates, so that even portions of the tissue specimen behind the coordinate markings can be viewed both optically and radiographically.

* * * * *